United States Patent [19]

Coy et al.

[11] Patent Number: 5,506,339
[45] Date of Patent: *Apr. 9, 1996

[54] OCTAPEPTIDE ANALOGS OF SOMATOSTATIN HAVING THREONINE AT THE SIXTH POSITION

[75] Inventors: David H. Coy, New Orleans; William A. Murphy, Covington, both of La.

[73] Assignee: The Administrators of the Tulane Educational Fund, New Orleans, La.

[*] Notice: The term of this patent shall not extend beyond the expiration date of Pat. No. 4,853,371.

[21] Appl. No.: 840,621

[22] Filed: Feb. 21, 1992

Related U.S. Application Data

[63] Continuation-in-part of Ser. No. 447,876, Dec. 8, 1989, abandoned.

[51] Int. Cl.$^6$ .................................................. C07K 14/655
[52] U.S. Cl. ........................ 530/311; 530/317; 530/328; 930/160; 930/260
[58] Field of Search .......................... 514/9, 2, 16, 806; 530/311, 317, 328; 930/160, 260

[56] References Cited

U.S. PATENT DOCUMENTS

| | | | |
|---|---|---|---|
| 4,282,143 | 8/1981 | Sarantakis | 530/311 |
| 4,291,022 | 9/1981 | Sandrin et al. | 424/177 |
| 4,328,135 | 5/1982 | Sarantakis | 525/54.11 |
| 4,395,403 | 7/1983 | Bauer et al. | 424/177 |
| 4,435,385 | 3/1984 | Bauer et al. | 424/177 |
| 4,485,101 | 11/1984 | Coy et al. | 424/177 |
| 4,650,787 | 3/1987 | Schally et al. | 530/311 |
| 4,684,620 | 8/1987 | Hurby et al. | 514/11 |
| 4,853,371 | 8/1989 | Coy et al. | 530/311 |
| 4,904,642 | 2/1990 | Coy et al. | 530/311 |
| 5,147,856 | 9/1992 | Ramwell et al. | 530/311 |

FOREIGN PATENT DOCUMENTS

| | | |
|---|---|---|
| 0203031 | 11/1986 | European Pat. Off. . |
| WO86/01516 | 3/1986 | WIPO . |

OTHER PUBLICATIONS

Verber et al., Life Sciences, 34:1371–1378 (1984).
Cai et al. (Jul. 1985) Proc. 9th Ann. Peptide Symposium Abstract, 627–630.
Schally et al., Proc. Natl. Acad. Sci. USA, 84:7275–7279 (1987).
Moreau et al., Life Sciences, 40:419–437 (1987).
Lamberts et al., European Journal of Clinical Investigation, Editorial, 17:281–287 (1987).
Siegel et al., Cancer Research, 48:4651–4655 (1988).
Cai et al, PNAS, vol. 83, (1986), pp. 1896–1900.
Murphy et al, Life Science, (1987), vol. 40 (26) pp. 2515–2522, (Chem. Abs. vol. 107, 147517k).
Hinby et al, Peptides, (1987), pp. 627–630.
Coy et al, Eur. Pat. App., 13 pp., (1987). [CA108(15), 132324s].
Michel et al, Pept. Proc. Eur. Pept. Symp., 18th, 585–9 (1984) [Chem. Abs. 103(13),98845x.

*Primary Examiner*—Jill Warden
*Assistant Examiner*—T. D. Wessendorf
*Attorney, Agent, or Firm*—Fish & Richardson; William E. McGowan

[57] ABSTRACT

A compound of the formula:

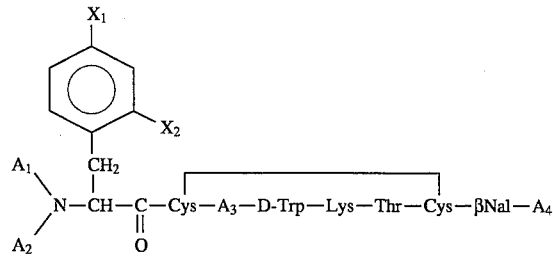

wherein each $A_1$ and $A_2$, independently, is H, $C_{1-12}$ alkyl, $C_{7-10}$ phenylalkyl, $R_1CO$ (where $R_1$ is $C_{1-20}$ alkyl, $C_{3-20}$ alkenyl, $C_{3-20}$ alkinyl, phenyl, naphthyl, or $C_{7-10}$ phenylalkyl), or $R_2OCO$ (where $R_2$ is $C_{1-10}$ alkyl or $C_{7-10}$ phenylalkyl), provided that when one of $A_1$ or $A_2$ is $R_1CO$ or $R_2OCO$, the other must be H;

each $X_1$ and $X_2$, independently, is H, F, Cl, Br, OH, $CH_3$, or $CF_3$, provided that at least one of $X_1$ and $X_2$ must be H;

$A_3$ is Phe or Tyr; and $A_4$ is OH, $NH_2$, or $NH-R_3$ (wherein $R_3$ is a saturated aliphatic $C_{1-8}$ alkyl);

or a pharmaceutically acceptable salt thereof. A therapeutic composition containing the compound of the present invention and a method of using the same are also described.

2 Claims, No Drawings

OCTAPEPTIDE ANALOGS OF SOMATOSTATIN HAVING THREONINE AT THE SIXTH POSITION

This invention was made in the course of work under a grant or award from the U.S. government; therefore, the U.S. government has rights in the invention.

This is a continuation-in-part of application Ser. No. 07/447,876, filed Dec. 8, 1989, now abandoned.

BACKGROUND OF THE INVENTION

This invention relates to therapeutic peptides.

A number of somatostatin analogs exhibiting growth hormone-release-inhibiting activity have been described in the literature, including analogs containing fewer than the naturally-occurring fourteen amino acids. For example, Coy et al., U.S. Pat. No. 4,485,101, hereby incorporated by reference, describes dodecapeptides having an amino-terminal acetyl group, a carboxy-terminal amino group, D-Trp at position 6, and p-Cl-Phe at position 4. (The name of each amino acid is herein designated by its standard three-letter abbreviation; the stereoisomeric designation of each amino acid is L unless otherwise specified.)

SUMMARY OF THE INVENTION

In general, the invention features a compound of the formula:

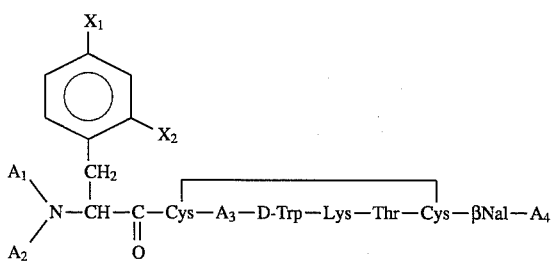

wherein
each $A_1$ and $A_2$, independently, is H, $C_{1-12}$ alkyl, $C_{7-10}$ phenylalkyl, $R_1CO$ (where $R_1$ is $C_{1-20}$ alkyl, $C_{3-20}$ alkenyl, $C_{3-20}$ alkinyl, phenyl, naphthyl, or $C_{7-10}$ phenylalkyl), or $R_2OCO$ (where $R_2$ is $C_{1-10}$ alkyl or $C_{7-10}$ phenylalkyl), provided that when one of $A_1$ or $A_2$ is $R_1CO$ or $R_2OCO$, the other must be H;

each $X_1$ and $X_2$, independently, is H, F, Cl, Br, OH, $CH_3$, or $CF_3$, provided that at least one of $X_1$ and $X_2$ must be H;

$A_3$ is Phe or Tyr; and $A_4$ is OH, $NH_2$, or $NH-R_3$ (wherein $R_3$ is a saturated aliphatic $C_{1-8}$ alkyl);

or a pharmaceutically acceptable salt thereof. The naturally-occurring amino acids are indicated by their generally-accepted three-letter symbols; unless the D-stereoisomer of an amino acid (other than βNal) is specified, the L-form is assumed. "βNal" denotes D- or L-β-naphthylalanine, unless the D- or L- stereoisomer is specified.

In preferred embodiments, each $A_1$ and $A_2$, independently, is H or a saturated aliphatic $C_{1-3}$ alkyl; each $X_1$ and $X_2$, independently, is H, F, Cl, or OH, provided that at least one of $X_1$ and $X_2$ must be H; and $R_3$ is a saturated aliphatic $C_{1-3}$ alkyl; more preferably, the compound has the formula:

or

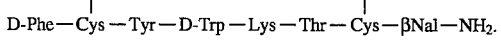

In another aspect, the invention features compounds of the formula:

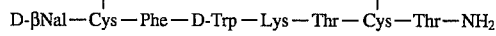

and

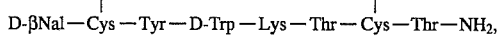

or a pharmaceutically acceptable salt thereof.

Recent studies have shown that

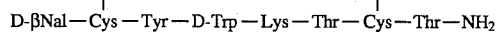

and

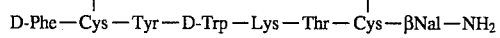

possess a longer-lasting activity in inhibiting stimulation of growth hormone release than somatostatin analogs which do not have a Thr residue at the 6th position, e.g.,

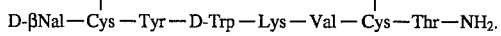

Also featured is a combination of one of the above compounds and a pharmaceutically acceptable carrier substance in a therapeutic composition capable of inhibiting the release of growth hormone ("GH"), epidermal growth factor, insulin, glucagon, pancreatic exocrine secretions, or substance P, and preferably of GH.

In preferred embodiments, the composition is in the form of a pill, tablet, capsule, or liquid for oral administration; a cream, gel, lotion, spray, or ointment for application to the skin of a patient; a liquid capable of being administered nasally as drops or spray; or a liquid capable of intravenous, subcutaneous, parenteral, or intraperitoneal administration. The therapeutic composition can also be in the form of an oil emulsion or dispersion in conjunction with a lipophilic salt such as a pamoic acid, or in the form of a biodegradable sustained-release formulation for subcutaneous or intramuscular administration. For maximum efficacy, zero-order release is desired. Zero-order release can be obtained using an implantable or external pump to administer the therapeutic composition.

The compounds of the invention exhibit a broad range of biological activities related to their antisecretory and antiproliferative properties. The compounds suppress the secretion of several endocrine hormones, including insulin, glucagon, and, in particular, growth hormone (GH). The compounds of the invention also suppress pancreatic and gastric exocrine secretions, and suppress or modulate the release of some neurotransmitters, including substance P and acetylcholine.

The somatostatin analogs can affect tumor cell multiplication by preventing the release of mitotic factors (such as insulin-like growth factor 1 (IGF-1), gastrin-releasing peptides, etc.), and may interfere with the intracellular transduction mechanism, as, for example, in the case of epidermal growth factor (EGF)-induced cell proliferation.

The aromatic lipophilic N-terminal end can provide long-lasting in vivo activity.

Other features and advantages of the invention will be apparent from the following description of the preferred embodiments thereof, and from the claims.

DESCRIPTION OF THE PREFERRED EMBODIMENTS

Structure

The compounds of the invention, which are peptide analogs of somatostatin, have the general formula recited in the Summary of the Invention, above.

The compounds can be provided in the form of pharmaceutically acceptable salts or complexes. As used herein, the term "pharmaceutically acceptable salts or complexes" refers to salts or complexes that retain the desired biological activity of the parent compound and do not impart any undesired toxicological effects. Examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with polyvalent metal cations such as zinc, calcium, bismuth, barium, magnesium, aluminum, copper, cobalt, nickel, cadmium, and the like, or with an organic cation formed from N,N-dibenzylethylene-diamine or ethylenediamine; or (c) combinations of (a) and (b): e.g., a zinc tannate salt or the like.

Synthesis

The synthesis of one octapeptide follows. Other compounds of the invention can be prepared by making appropriate modifications, within the ability of someone of ordinary skill in this field, of the following synthetic method.

The first step in the preparation of

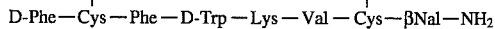
D-Phe—Cys—Phe—D-Trp—Lys—Val—Cys—βNal—NH₂ was the preparation of the intermediate tert-butyloxycarbonyl -D-Phe-S-methylbenzyl-Cys-Phe-D-Trp-Nᵋ-benzyloxycarbonyl -Lys-Thr-S-methylbenzyl-Cys-βNal-NH₂-benzyhydrylamine resin, as follows.

Methyl-benzhydrylamine-polystyrene resin (Advanced Chem-Tech, Inc.) in the chloride ion form was placed in the reaction vessel of a Beckman 990B peptide synthesizer programmed to perform the following reaction cycle: (a) methylene chloride; (b) 33% trifluoroacetic acid in methylene chloride (2 times for 1 and 25 min each); (c) methylene chloride; (d) ethanol; (e) methylene chloride; (f) 10% triethylamine in chloroform.

The neutralized resin was stirred with Boc-βNal and diisopropylcarbodiimide (1.5 mmole each) in methylene chloride for 1 h and the resulting amino acid resin was then cycled through steps (a) to (f) in the above wash program. The following amino acids (1.5 mmole) were then coupled successively by the same procedure: Boc-S-methylbenzyl-Cys, Boc-Thr, Boc-Nᵋ -benzyloxycarbonyl-Lysine, Boc-D-Trp, Boc-Phe, Boc-S-methylbenzyl-Cys, Boc-D-Phe.

The resin was washed and dried and then mixed with anisole (4 ml) and anhydrous hydrogen fluoride (36 ml) at 0° C. and stirred for 45 min. (one can also use thioanisole, trifluoroacetic acid, and trifluoromethane sulfonic acid at a ratio of 1:90:9, for 6 h). Excess hydrogen fluoride was evaporated rapidly under a stream of dry nitrogen and free peptide precipitated and washed with ether. The crude peptide was then dissolved in 800 ml of 90% acetic acid, to which was added I₂ in methanol until a permanent brown color was present. The solution was then stirred for 1 h before removing the solvent in vacuo. The resulting oil was dissolved in a minimum volume of 50% acetic acid and eluted on a column (2.5×100 mm) of Sephadex G-25. Fractions containing a major component by UV absorption and thin-layer chromatography were then pooled, evaporated to a small volume, and applied to a column (2.5×50 cm) of Vydac octadecylsilane (10–15 µM).

The column was eluted with a linear gradient of 10–50% acetonitrile in 0.1% trifluoroacetic acid in water. Fractions were examined by thin-layer chromatography and analytical high-performance liquid chromatography, pooled to give maximum purity, and, if desired, a different salt prepared, e.g., acetate or phosphate. Repeated lyophilization of the solution from water gave 120 mg of the product as a white, fluffy powder.

The product was found to be homogeneous by high-performance liquid chromatography and thin-layer chromatography. Amino acid analysis of an acid hydrolysate confirmed the composition of the octapeptide.

Compounds of the invention having the formulas

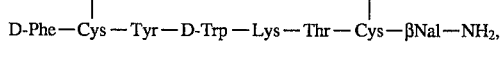
D-Phe—Cys—Tyr—D-Trp—Lys—Thr—Cys—βNal—NH₂,

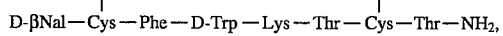
D-βNal—Cys—Phe—D-Trp—Lys—Thr—Cys—Thr—NH₂, and

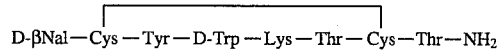
D-βNal—Cys—Tyr—D-Trp—Lys—Thr—Cys—Thr—NH₂ were made according to methods analogous to those described above.

Use

When administered to mammals, particularly humans (e.g. orally; topically; intravenously; parenterally in a sustained release, biodegradable form; nasally; or by suppository), the compounds can be effective to inhibit the secretion of various hormones and trophic factors. They may be used to suppress certain endocrine secretions, such as GH, insulin, glucagon and prolactin, in the treatment of, for example, acromegaly; endocrine tumors such as carcinoids, vipomas, insulinomas, and glucagonomas; or diabetes and diabetes-related pathologies, including retinopathy, nephropathy, dawn syndrome and type 2 diabetes. The compounds may also be used to suppress exocrine secretions in the pancreas, stomach and intestines, for treatment of, for example, pancreatitis, fistulas, bleeding ulcers, and diarrhea associated with such diseases as AIDS or cholera. Disorders involving autocrine or paracrine secretions of trophic factors such as IGF-1 (as well as some endocrine factors) which may be treated by administration of these compounds include cancers of the breast, prostate, and lung (both small cell and non-small cell epidermoids), as well as hepatomas, neuroblastomas, colon and pancreatic adenocarcinomas (ductal type), chondrosarcomas, and melanomas, and also atherosclerosis associated with vascular grafts and restenosis following angioplasty.

The compounds of the invention also are useful to suppress the mediators of neurogenic inflammation (e.g., substance P or the tachykinins), and thus may be used in the treatment of such pathologies as rheumatoid arthritis; psoriasis; topical inflammation such as is associated with sunburn, eczema, or other sources of itching; and allergies, including asthma. The compounds also can function as neuromodulators in the central nervous system, with useful applications in the treatment of Alzheimer's disease and other forms of dementia, pain (as a spinal analgesic), and headaches. Furthermore, in disorders involving the splanchnic blood flow, including cirrhosis, oesophagal varices, and certain cases of mushroom poisoning, the compounds of the invention can provide cytoprotection.

The compounds can be administered to a mammal, e.g., a human, in a dosage of 0.01 to 50 mg/kg/day, preferably 0.1 to 5 mg/kg/day.

Other embodiments are within the following claims.

We claim:

1. A compound of the formula:

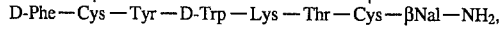

or a pharmaceutically acceptable salt thereof.

2. A compound of the formula:

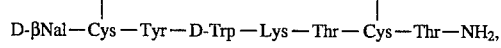

or a pharmaceutically acceptable salt thereof.

* * * * *

UNITED STATES PATENT AND TRADEMARK OFFICE
CERTIFICATE OF CORRECTION

PATENT NO.    : 5,506,339

DATED         : April 09, 1996

INVENTOR(S)   : David H. Coy and William A. Murphy

It is certified that error appears in the above-identified patent and that said Letters Patent is hereby corrected as shown below:

On the title page item,
[75] change "Covington" to --"Slidell"--

Signed and Sealed this

Nineteenth Day of August, 1997

Attest:

BRUCE LEHMAN

Attesting Officer    Commissioner of Patents and Trademarks